United States Patent
Machhammer et al.

(10) Patent No.: US 6,781,017 B2
(45) Date of Patent: Aug. 24, 2004

(54) METHOD FOR THE PRODUCTION OF ACROLEIN OR ACRYLIC ACID OR THE MIXTURE THEREOF FROM PROPANE

(75) Inventors: Otto Machhammer, Mannheim (DE); Goetz-Peter Schindler, Mannheim (DE); Andreas Tenten, Maikammer (DE); Klaus Harth, Altleiningen (DE); Peter Zehner, Ludwigshafen (DE); Klaus Joachim Müller-Engel, Stutensee (DE); Frank Rosowski, Mannheim (DE); Frieder Borgmeier, Mannheim (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/297,602

(22) PCT Filed: Jun. 8, 2001

(86) PCT No.: PCT/EP01/06528
§ 371 (c)(1),
(2), (4) Date: Dec. 13, 2002

(87) PCT Pub. No.: WO01/96270
PCT Pub. Date: Dec. 20, 2001

(65) Prior Publication Data
US 2003/0181762 A1 Sep. 25, 2003

(30) Foreign Application Priority Data
Jun. 14, 2000 (DE) .......................................... 100 28 582

(51) Int. Cl.$^7$ .............................................. C07C 45/00
(52) U.S. Cl. ...................... 568/470; 568/475; 568/476; 562/512.2; 562/530
(58) Field of Search ................... 568/470, 475, 568/476; 562/512.2, 530

(56) References Cited

U.S. PATENT DOCUMENTS

| | | | |
|---|---|---|---|
| 3,161,670 A | | 12/1964 | Adams et al. |
| 4,788,371 A | * | 11/1988 | Imai et al. ................. 585/443 |
| 5,198,578 A | | 3/1993 | Etzkorn et al. |

FOREIGN PATENT DOCUMENTS

| | | |
|---|---|---|
| DE | 33 13 573 | 10/1983 |
| DE | 195 08 558 | 9/1996 |
| DE | 196 22 331 | 12/1997 |
| DE | 198 37 517 | 2/2000 |
| DE | 198 37 519 | 2/2000 |
| DE | 198 37 520 | 2/2000 |
| EP | 0 117 146 | 8/1984 |
| EP | 0 731 077 | 9/1996 |
| EP | 0 731 082 | 9/1996 |
| GB | 2 118 939 | 11/1983 |
| JP | 11-035519 | 2/1999 |
| SU | 193484 | 3/1966 |

* cited by examiner

Primary Examiner—S. Kumar
Assistant Examiner—Sikarl A. Witherspoon
(74) Attorney, Agent, or Firm—Oblon, Spivak, McClelland, Maier & Neustadt, P.C.

(57) ABSTRACT

In a process for the preparation of acrolein or acrylic acid or a mixture thereof from propane, the propane is subjected, in a first reaction stage, to a partial dehydrogenation under heterogeneous catalysis to give propene, of the components contained in the product gas mixture formed in the first reaction stage other than propene and propane at least a portion of the molecular hydrogen present is then separated off from said mixture and the product gas mixture is then used for the preparation of acrolein and/or acrylic acid by gas-phase catalytic propylene oxidation, molecular nitrogen being present for diluting the reaction gas mixture during the propylene oxidation.

49 Claims, No Drawings

METHOD FOR THE PRODUCTION OF ACROLEIN OR ACRYLIC ACID OR THE MIXTURE THEREOF FROM PROPANE

The present invention relates to a process for the preparation of acrolein or acrylic acid or a mixture thereof from propane, in which A) in a first stage A, the propane is subjected to a partial dehydrogenation under heterogeneous catalysis in the gas phase with formation of a product gas mixture A which contains molecular hydrogen, propylene and unconverted propane, B) of the components contained in the product gas mixture A and differing from propane and propylene, at least a portion of the molecular hydrogen is separated off from said mixture A of stage A, containing molecular hydrogen, propylene and unconverted propane, the mixture is then used as product gas mixture A' in a second stage B for feeding at least one oxidation reactor and, in the at least one oxidation reactor, the propylene is subjected to a selective partial gas-phase oxidation with molecular oxygen under heterogeneous catalysis to give a product gas mixture B which contains acrolein or acrylic acid or a mixture thereof as the desired product, and C) in a third stage C, the desired product is separated off from the product gas mixture B obtained in the partial oxidation of the propylene in stage B and at least unconverted propane contained in the product gas mixture of stage B is recycled to the dehydrogenation stage A.

Acrylic acid is a key chemical which is used, inter alia, as a monomer for the preparation of polymers which are used as binders, for example in the form of a dispersion in an aqueous medium. Acrolein is a key intermediate, for example for the preparation of glutardialdehyde, methionine, folic acid and acrylic acid.

EP-A 117 146, DE-A 3 313 573 and U.S. Pat. No. 3,161,670 disclose a process for converting propane into acrolein and/or acrylic acid (below, reference is made only to EP-A 117 146 as representative).

In a first process stage, the propane is subjected to a partial dehydrogenation in the gas phase under heterogeneous catalysis. The propylene formed is then subjected, in a second process stage, to a partial gas-phase oxidation under heterogeneous catalysis to give acrolein and/or acrylic acid. A typical feature of EP-A 117 146 is that the main components present in the product gas mixture of propane dehydrogenation in addition to propylene, such as molecular hydrogen, are essentially inert with respect to the subsequent partial gas-phase oxidation of the propylene under heterogeneous catalysis, so that the product gas mixture of the propane dehydrogenation according to EP-A 117 146 can be transferred without substantial disadvantages in its entirety to the subsequent propylene oxidation stage and, of the inert components, at least the unconverted propane can then be recycled to the propane dehydrogenation stage.

DE-A 19 508 558 shows that EP-A 117 146 is disadvantageous in that it states that the presence of inert diluent gases different from propane in the second process stage of EP-A 117 146 is disadvantageous. A typical feature of DE-A 19 508 558 therefore comprises separating off at least the molecular hydrogen and the steam from the product gas mixture of the first process stage of EP-A 117 146 before it is further used in the second process stage and using pure oxygen as an oxygen source for the second process stage.

As a result of intensive research activity, however it was found that the procedure recommended in DE-A 19 508 558 in the second process stage results in increased byproduct formation in the form of propionaldehyde and/or propionic acid. The latter is disadvantageous in that (cf. for example Japanese Laid Open Patent Application No. H11-35519), on the one hand, the saturated partial $C_3$ oxidation byproducts are very difficult to separate from the desired $\alpha,\beta$-ethylenically unsaturated desired partial $C_3$ oxidation products, owing to their chemical similarity, and, on the other hand, owing to their penetrant odor, are very troublesome even in very small amounts when the desired partial $C_3$ oxidation products are marketed.

It is an object of the present invention to provide a procedure which is improved in comparison with the procedure of EP-A 117 146 and of DE-A 19 508 558.

In this respect, for example, the procedures of DE-A 19 837 517, of DE-A 19 837 519 and of DE-A 19 837 520, in which the process step of the partial dehydrogenation under heterogeneous catalysis is replaced by a partial oxydehydrogenation under homogeneous and/or heterogeneous catalysis, are unsatisfactory (although the resulting dehydrogenation mixture does not contain hydrogen) since they require the presence of considerable amounts of molecular oxygen even in the dehydrogenation stage.

We have found that this object is achieved by a process for the preparation of acrolein or acrylic acid or a mixture thereof from propane, in which A) in a first stage A, the propane is subjected to a partial dehydrogenation under heterogeneous catalysis in the gas phase with formation of a product gas mixture A which contains molecular hydrogen, propylene and unconverted propane, B) of the components contained in the product gas mixture A and differing from propane and propylene, at least a portion of the molecular hydrogen is separated off from said mixture A of stage A, containing molecular hydrogen, propylene and unconverted propane, the mixture is then used as product gas mixture A' in a second stage B for feeding at least one oxidation reactor and, in the at least one oxidation reactor, the propylene is subjected to a selective partial gas-phase oxidation with molecular oxygen under heterogeneous catalysis to give a product gas mixture B which contains acrolein and or acrylic acid or a mixture thereof as the desired product, and C) in a third stage C, the desired product is separated off from the product gas mixture B obtained in the partial oxidation of the propylene in stage B and at least unconverted propane contained in the product gas mixture of stage B is recycled to the dehydrogenation stage A, wherein molecular nitrogen is present as diluent gas in the partial oxidation of the propylene in stage B.

This means that, whereas feed gas which essentially comprises only propylene, molecular oxygen and propane is fed to oxygen stage B according to DE-A 19 508 558, the feed gas which necessarily contains propylene, molecular oxygen, propane and molecular nitrogen is fed to the oxidation stage B in the novel procedure. The choice of the abovementioned components of the feed gas mixture of oxidation stage B ensures that, in the novel procedure, not only is a feed gas mixture whose limiting oxygen concentration (regarding the definition, cf. DE-A 19 508 558) is completely satisfactory in terms of application technology fed to oxidation stage B but said feed gas mixture simultaneously permits a reduction in the formation of the undesired byproducts propionaldehyde and/or propionic acid.

Of course, the feed gas mixture of oxidation stage B in the novel procedure may contain, in addition to the abovementioned components, also other components, e.g. CO, $CO_2$, $H_2O$, noble gases such as He and/or Ar, hydrogen, methane, ethylene, ethane, butanes, butenes, butynes, pentanes, propyne, allenes and/or acrolein. As a rule, the proportion of molecular oxygen in the feed gas mixture of oxidation stage B should be, according to the invention not less than 5 mol %, based on the amount of propylene contained in the feed gas mixture. This means that, in the novel process, the proportion of molecular oxygen in the feed gas mixture of oxidation stage B may be at least 10 mol % or at least 15 mol % or at least 20 mol % or at least 25 mol % or at least 50 mol %, but also at least 100 mol % or at least 200 mol % or at least 500 mol % or at least 750 mol % or at least 1000 mol %, based on the amount of propylene present. According to the invention, the ratio of the molar amount of molecular nitrogen contained in the feed gas mixture of oxidation stage B to the molar amount of propylene contained in the said mixture is however usually $\leq 40:1$, frequently $\leq 30:1$, in many cases $\leq 20:1$ and often $\leq 10:1$. It is advantageous if, in the novel process, the proportion of molecular nitrogen in the feed gas mixture of oxidation stage B is from 600 to 1600 mol %, based on the amount of propylene present.

The molar ratio of the amount of molecular nitrogen contained in the feed gas mixture of oxidation stage B to the amount of propane contained in the said mixture is as a rule not less than 0.05 in the novel process. Usually, however, this ratio is also not above five, i.e., according to the invention, the molar ratio of the amount of molecular nitrogen contained in the feed gas mixture of oxidation stage B to the amount of propane contained in said mixture may be from 0.05 to 5, or from 0.1 to 4, or from 0.5 to 3, or from 1 to 2.5, or about 2.

In the novel process, the composition of the feed gas mixture of oxidation stage B is frequently chosen so that it complies with the following molar ratios:

Propane:propene:$N_2$:$O_2$:$H_2O$:other substances=from 0.5 to 20:1: from 0.1 to 40: from 0.1 to 10: from 0 to 20: from 0 to 1.

According to the invention, the abovementioned molar ratios are advantageously from 2 to 10:1: from 0.5 to 20: from 0.5 to 5: from 0.01 to 10: from 0 to 1.

It is also advantageous according to the invention if the abovementioned molar ratios are from 3 to 6:1: from 1 to 10: from 1 to 3: from 0.1 to 2 from 0 to 0.5.

An essential feature of the novel procedure is that the product gas mixture A of stage A, in contrast to the partial oxydehydrogenation of propane under homogeneous and/or heterogeneous catalysis, contains molecular hydrogen and that, before the product gas mixture A is used for feeding the at least one oxidation reactor of stage B, at least a portion of this molelcular hydrogen is separated off from the product gas mixture A in contrast to EP-A 117 146, and, in contrast to DE-A 19 508 558, is replaced by molecular nitrogen to reduce the propionaldehyde and/or propionic acid byproduct formation.

In the novel process the molar ratio of the propylene contained in the product gas mixture A to the molecular hydrogen contained in said mixture is $\leq 100$, usually $\leq 75$, frequently $\leq 50$, often $\leq 40$, in many cases $\leq 30$, or $\leq 25$ or $\leq 20$.

This means that novel processes include in particular those in which the molar ratio of propylene contained in the product gas mixture A to molecular hydrogen contained in said mixture is $\leq 15$ or $\leq 10$ or $\leq 5$ or $\leq 3$ or $\leq 2$ or $\leq 1$.

Usually, the reciprocal value of the abovementioned ratio does not exceed 20.

This means that in the novel process, the molar ratio of propylene contained in the product gas mixture A to molecular hydrogen contained in said mixture is usually $\geq 0.05$, in general $\geq 0.025$, often $\geq 0.1$, frequently $\geq 0.25$, in many cases $\geq 0.5$ or $\geq 0.75$ or $\geq 0.9$.

In order to achieve conversions of interest, based on a single pass, in stage A in the partial dehydrogenation carried out according to the invention on heterogeneous catalysis, as a rule relatively high reaction temperatures have to be employed (typically, these reaction temperatures are from 300 to 700° C.). Since the dehydrogenation (cleavage of C—H) is kinetically disadvantageous compared with cracking (cleavage of C—C), it takes place over selective catalysts. As a rule, one hydrogen molecule is produced as a byproduct per propylene molecule formed. Owing to the selective catalysts, which are usually such that they display significant dehydrogenation in the absence of oxygen at the abovementioned temperatures (e.g. at 600° C.) (in which case propane loadings of the catalysts of, for example 1000 $h^{-1}$, the propylene used is generally at least 30 mol % in a single pass (based on propane used)), byproducts such as methane, ethylene and ethane form only in minor amounts.

Since the dehydrogenation reaction takes place with an increase in volume, the conversion can be increased by reducing the partial pressure of the products. This can be achieved in a simple manner, for example by dehydrogenation at reduced pressure and/or by admixing essentially inert diluents, e.g. steam, which is usually an inert gas for the dehydrogenation reaction. Dilution with steam has a further advantage that there is generally reduced coking of the catalyst used since the steam reacts with the coke formed according to the principle of coal gasification. In addition, steam can be present as a diluent gas in the subsequent oxidation stage B. However, steam can also be easily separated off partially or completely from the product gas mixture A of the novel process stage A (for example by condensation), which makes it possible, when the product gas mixture A' obtainable is further used in the oxidation stage B, to increase the proportion of the diluent gas $N_2$ essential for the invention. According to the invention, it is entirely possible concomitantly to use the total amount or only a portion of the molecular nitrogen which is to be present according to the invention in the oxidation stage B also for dilution in stage A. Further diluents suitable for stage A are, for example, CO, $CO_2$ and noble gases, such as He, Ne and Ar. All stated diluents may be present in stage A either by themselves or in the form of different mixtures. According to the invention, it is advantageous if the diluents suitable for stage A are as a rule also diluents suitable for oxidation stage B. In general, diluents which are inert in the respective stage (i.e. chemical change of less than 5, preferably less than 3, more preferably less than 1, mol %) are preferred. In principle, all the hydrogenation catalysts known in the prior art are suitable for the novel stage A. They can be generally divided into two groups, i.e. into those which are of oxidic nature (e.g. chromium oxide and/or alumina) and those which consist of at least one metal, as a rule comparatively noble (e.g. platinum), deposited on a support, as a rule an oxidic one.

Inter alia, all dehydrogenation catalysts which are recommended in WO 99/46039, U.S. Pat. No. 4,788,371, EP-A 705 136, WO 99/29420, U.S. Pat. No. 5,220,091, 5,430,220, 5,877,369, EP-A 117 146, DE-A 19 937 106, DE-A 19 937 105 and DE-A 19 937 107 can thus be used for the novel stage A. In particular the catalyst according to Example 1, that according to Example 2, that according to Example 3 and that according to Example 4 of DE-A 19 937 107 can be used for all dehydrogenation process variants discussed in this publication as being suitable for the novel stage A.

These are dehydrogenation catalysts which contain from 10 to 99.9% by weight of zircondium dioxide, from 0 to 60% by weight of alumina, silica and/or titanium dioxide and from 0.1 to 10% by weight of at least one element of the first or second main group, one element of the third subgroup, one element of the eighth subgroup of the Periodic Table of the Elements, lanthanum and/or tin, with the proviso that the sum of the percentages by weight is 100% by weight.

In principle, all reactor types and process variants known in the prior art are suitable for carrying out stage A of the novel process. For example, all prior art publications mentioned with regard to the dehydrogenation catalysts contain descriptions of such process variants.

A comparatively detailed description of dehydrogenation processes suitable according to the invention is also contained in Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.

Typical of the partial dehydrogenation of propane under heterogeneous catalysis is that it is endothermic, i.e. the heat (energy) necessary for establishing the required reaction temperature must be supplied either to the reaction just beforehand and/or in the course of the catalytic dehydrogenation.

Also typical of dehydrogenations of propane under heterogeneous catalysis, owing to the high reaction temperatures required, is that high-boiling high molecular weight organic compounds, including carbon, are formed in small amounts and deposited on the catalyst surface and thus deactivate it. In order to minimize this advantageous accompanying phenomenon, it is possible, as stated above, to dilute with steam the propane to be passed for catalytic dehydrogenation at elevated temperatures over the catalyst surface. Under the resulting conditions, carbon deposited is partially or completely eliminated according to the principle of coal gasification.

Another possibility for eliminating deposited carbon compounds comprises passing an oxygen-containing gas through the dehydrogenation catalyst from time to time at elevated temperature and thus, so to speak, separating off the deposited carbon. Suppression of the formation of carbon deposits is however also possible by adding molecular hydrogen to the propane to be dehydrogenated catalytically, before it is passed at elevated temperature over the dehydrogenation catalyst.

Of course, it is also possiblie to add steam and molecular hydrogen as a mixture to the propane to be dehydrogenated catalytically. Addition of molecular hydrogen to the catalytic dehydrogenation of propane also reduces the undesired formation of allene and acetylene as byproducts.

A suitable reactor form for the novel stage A is fixed-bed tubular reactor or tube-bundle reactor, i.e. the dehydrogenation catalyst is present as a fixed bed in a reaction tube or in a bundle of reaction tubes. The reaction tubes are heated by combustion of a gas, for example a hydrocarbon, such as methane, in the space surrounding the reaction tubes. It is advantageous to apply this direct form of heating the catalyst tubes only to the first about 20 to 30% of the fixed bed and to heat the remaining bed length to the required reaction temperature by means of the radiant heat evolved in the course of the combustion. In this way, a virtually isothermal reaction procedure can be achieved. Suitable reaction tube internal diameters are from about 10 to 15 cm. A typical dehydrogenation tube bundle reactor comprises from 300 to 1000 reaction tubes. The temperature in the interior of the reaction tube is from 300 to 700° C., preferably from 400 to 700° C. Advantageously, the reaction gas is preheated to the reaction temperature before being fed to the tubular reactor. Frequently, the product gas mixture leaves the reaction tube at a temperature which is from 50 to 100° C. lower. In the abovementioned procedure, the use of oxidic dehydrogenation catalysts based on chromium oxide and/or alumina is expedient. Frequently, no diluent gas is present; instead, essentially pure propane is used as starting reaction gas. The dehydrogenation catalyst, too, is generally used undiluted.

On an industrial scale, about three tube-bundle reactors would be operated in parallel, and two of these reactors would generally be operated in the dehydrogenation mode while the catalyst load is regenerated in one of the reactors.

The above procedure is used, for example, in the BASF-Linde propane dehydrogenation process known in the literature.

Furthermore, it is used in the steam active reforming (STAR) process, which was developed by Philips Petroleum Co. (cf. for example U.S. Pat. Nos. 4,902,849, 4,996,387 and 5,389,342). Promoter-containing platinum on zinc (magnesium) spinel as a support is advantageously used as a dehydrogenation catalyst in the STAR process (cf. for example U.S. Pat. No. 5,073,662). In contrast to the BASF-Linde propane dehydrogenation process the propane to be dehydrogenated is diluted with steam in the STAR process. A molar ratio of steam to propane of from 4 to 6 is typical. The operating pressure is frequently from 3 to 8 atm and the reaction temperature is expediently chosen to be from 480 to 620° C. Typical catalyst loadings with a total reaction gas mixture are from 0.5 to 10 $h^{-1}$.

Of course, the novel stage A can also be designed in the form of a moving bed. For example, the moving catalyst bed can be housed in a radial flow reactor. The catalyst moves slowly therein from top to bottom while the reaction gas mixture flows radially. This procedure is used, for example, in the UOP Oleflex dehydrogenation process. Since in this process the reactors are operated virtually adiabatically, it is expedient to operate a plurality of reactors connected in series (typically up to four). This makes it possible to avoid excessively large differences between the temperature of the reaction gas mixture at the reactor inlet and at the reactor outlet (in the adiabatic mode of operation the reaction gas starting mixture acts as a heat-transfer medium, on the heat content of which the reaction temperature depends) and nevertheless to achieve attractive overall conversions.

When the catalyst bed has left the moving-bed reactor it is fed for regeneration and then reused. For example, a spherical dehydrogenation catalyst which essentially comprises platinum on a spherical alumina support can be used as dehydrogenation catalyst for this process. In the UOP variant, hydrogen is added to the propane to be dehydrogenated, in order to avoid premature aging of the catalyst. The operating pressure is typically from 2 to 5 atm. The molar hydrogen-to-propane ratio is expediently from 0.1 to 1. The reaction temperatures are preferably from 550 to 650° C. and the catalyst loading with reaction gas mixture is chosen to be about 2 to 6 $h^{-1}$.

In the fixed-bed process described, the catalyst geometry may likewise be spherical but may also be cylindrical (hollow or solid).

As a further process variant for the novel stage A, Proceedings De Witt, Petrochem. Review, Houston Tex., 1992 a, N1, describes the possibility of a propane dehydrogenation under heterogeneous catalysis in a fluidized bed, in which the propane is not diluted.

Here, expediently two fluidized beds are operated side by side, one of which is generally in the regeneration state. The active material used is chromium oxide on alumina. The operating pressure is typically from 1 to 1.5 atm and the dehydrogenation temperature is as a rule from 550 to 600° C. The heat required for the dehydrogenation is introduced into the reaction system by preheating the dehydrogenation catalyst to the reaction temperature. The operating pressure is usually from 1 to 2 atm and the reaction temperature is typically from 550 to 600° C. The above dehydrogenation method is also known in the literature as the Snamprogetti-Yarsintez process.

Alternatively to the procedures described above, the novel stage A can also be realized according to a process developed by ABB Lummus Crest (cf. Proceedings De Witt, Petrochem. Review, Houston Tex., 1992, P1).

A common feature of the propane dehydrogenation processes under heterogeneous catalysis which have been described to date is that they are operated at propane conversions of >30 mol % (as a rule $\leq 60$ mol %) (based on a single reactor pass).

An advantage according to the invention is the fact that it is sufficient for the novel process to achieve, in stage A, a propane conversion of $\geq 5$ to $\leq 30$ mol % or $\leq 25$ mol %. This means that, according to the invention, stage A can also be operated at propane conversions of from 10 to 20 mol % (the conversions are based on a single reactor pass). This is due, inter alia, to the fact that the remaining amount of unconverted propane is diluted with molecular nitrogen in the subsequent oxidation stage B, which reduces the propionaldehyde and/or propionic acid byproduct formation.

In order to realize the abovementioned propane conversions, it is advantageous to carry out the novel propane dehydrogenation in stage A at an operating pressure of from 0.3 to 2 atm. Furthermore, it is advantageous if the propane to be dehydrogenated is diluted with steam. Thus, on the one hand, the heat capacity of the water makes it possible to compensate same of the effect of the endothermic nature of the dehydrogenation and, on the other hand, the dilution with steam reduces the partial pressure of starting materials and product, which has an advantageous effect on the equilibrium position of the dehydrogenation. Furthermore, as stated above, the presence of steam has an advantageous effect on the on-stream time of the dehydrogenation catalyst. If required, molecular hydrogen may also be added as a further component. The molar ratio of molecular hydrogen to propane is as a rule $\leq 5$. Accordingly, in the stage A variant with comparatively low propane conversion of from $\geq 0$ to 30, the molar ratio of steam to propane may be expediently from 0.1 to 2, advantageously from 0.5 to 1. It also proves advantageous to proceed at low propane conversion but, in a single pass of the reaction gas through the reactor, only a comparatively small amount of heat is consumed and comparatively low reaction temperatures are sufficient for achieving the conversion in a single reactor pass.

It is therefore expedient according to the invention to carry out the propane dehydrogenation (virtually) adiabatically in the stage A variant with comparatively low propane conversion. This means that the reaction gas starting mixture is as a rule heated to a temperature of from 500 to 700° C. (for example by direct heating of the surrounding wall) or to from 550 to 650° C. Usually a single adiabatic pass through a catalyst bed is then sufficient for achieving the desired conversion, the reaction gas mixture being cooled by from about 30° C. to 200° C. (depending on conversion). The presence of steam as a heat-transfer medium is also advantageous from the point of view of an adiabatic procedure. The lower reaction temperature permits longer on-stream times of the catalyst bed used.

In principle, the novel stage A variant with comparatively low propane conversion can also be carried out, either adiabatically or isothermally, both in a fixed-bed reactor and in a moving-bed or fluidized-bed reactor.

It is noteworthy that for realizing the said variant, in particular in adiabatic operation, a single shaft reactor is sufficient as fixed-bed reactor, through which reactor gas mixture flows axially and/or radially.

In the simplest case, this is a single reaction tube whose internal diameter is from 0.1 to 10 m, possibly also from 0.5 to 5 m, and in which the fixed catalyst bed is mounted on a support apparatus (for example a grid). The reaction tube which is loaded with catalyst and is heat-insulated in adiabatic operation is flowed through axially by the hot, propane-containing reaction gas. The catalyst geometry may be either spherical or annular. In the abovementioned case, however, the catalyst can advantageously also be used in the form of chips. In order to realize a radial flow of the propane-containing reaction gas, the reactor may consist of, for example, two cylindrical grids present in a jacket and arranged concentrically one inside the other, and the catalyst bed may be arranged in their annular gaps. In the adiabatic case, the jacket in turn would be thermally insulated.

A particularly suitable catalyst load for the novel stage A variant with comparatively low propane conversion in a single pass comprises the catalysts disclosed in DE-A 19 937 107, especially all those disclosed by way of example.

After prolonged operation, the abovementioned catalysts can be regenerated, for example, in a simple manner in which first, in first regeneration stages, air diluted with nitrogen is passed over the catalyst bed at from 300 to 600° C., frequently from 400 to 500° C. The catalyst loading with regenerating gas can be, for example, from 50 to 10000 $h^{-1}$ and the oxygen content of the regenerating gas may be from 0.5 to 20% by volume.

In downstream further regeneration stages, air may be used as regenerating gas under otherwise identical regeneration conditions. It is expedient in terms of application technology to flush the catalyst with inert gas (e.g. $N_2$) before its regeneration.

It is then generally advisable also to carry out regeneration with pure molecular hydrogen or with molecular hydrogen diluted with inert gas (the hydrogen content should be $\geq 1$% by volume) under otherwise identical conditions.

The novel stage A variant with comparatively low propane conversion ($\leq 30$ mol %) can be operated in all cases at the same catalyst loadings (relating to both the reaction gas as a whole and the propane contained therein) as the variants with high propane conversion (>30 mol %). This loading with reaction gas may be, for example, from 100 to 10000 $h^{-1}$, frequently from 100 to 3000 $h^{-1}$, i.e. in many cases from about 100 to 2000 $h^{-1}$.

The novel stage A variant with comparatively low propane conversion can be realized in a particularly elegant manner in a tray reactor.

This contains, spatially in succession, more than one catalyst bed catalyzing the dehydrogenation. The number of catalyst beds may be from 1 to 20, expediently from 2 to 8, but also from 4 to 6. The catalyst beds are preferably arranged radially or axially one behind the other. It is expedient in terms of application technology to choose the fixed-bed catalyst type in such a tray reactor.

In the simplest case, the fixed catalyst beds are arranged in a shaft reactor axially or in the annular gaps of cylindrical grids positioned concentrically one inside the other.

In an expedient manner, the reaction gas mixture is subjected to intermediate heating in the tray reactor on its way from one catalyst bed to the next, for example by passing over heat-exchanger ribs heated with hot gases or by passing through tubes heated with hot combustion gases.

If otherwise the tray reactor is operated adiabatically, it is sufficient for the desired propane conversion ($\leq 30$ mol %), particularly with the use of the catalysts described in DE-A 19 937 107, in particular the exemplary embodiments, if the reaction gas mixture is preheated to a temperature of from 450 to 550° C. before being fed into the dehydrogenation reactor and is kept in this temperature range within the tray reactor. This means that the total propane dehydrogenation is realized in this way at extremely low temperature which is particularly advantageous for the on-stream time of the fixed catalyst beds.

It is even more elegant to carry out the intermediate heating described above by direct methods. For this purpose, a limited amount of molecular oxygen is added to the reaction gas mixture before it flows through the first catalyst bed and/or between the downstream catalyst beds. Depending on the dehydrogenation catalyst used, limited combustion of the hydrocarbons contained in the reaction gas mixture, of any carbon or carbon-like compounds deposited on the catalyst surface and/or of hydrogen formed in the course of the propane dehydrogenation and/or added to the reaction gas mixture is thus effected (it may also be expedient in terms of application technology to introduce into the tray reactor catalyst beds which are loaded with catalyst which specifically (selectively) catalyzes the combustion of hydrogen (and/or of hydrocarbon) (examples of suitable catalysts of this type are those of U.S. Pat. Nos. 4,788,371, 4,886,928, 5,430,209, 5,530,171, 5,527,979 and U.S. Pat. No. 5,563,314); for example, such catalyst beds could be housed in the tray reactor in an alternating manner with the beds containing the dehydrogenation catalyst). The heat of reaction evolved thus permits, in a virtually autothermal manner, virtually isothermal operation of the propane dehydrogenation under heterogeneous catalysis. As the chosen residence time of the reaction gas in the catalyst bed increases, it is thus possible to carry out a propane dehydrogenation at a lower and essentially constant temperature, which permits particularly long on-stream times.

As a rule, an oxygen feed as described above should be carried out in such a way that the oxygen content of the reaction gas mixture is from 0.5 to 10% by volume, based on the amount of propane and propylene contained therein. A suitable oxygen source is either pure molecular oxygen or oxygen diluted with inert gas, e.g. CO, $CO_2$, $N_2$, or noble gases, but in particular air. The resulting combustion gases generally have an additional diluting effect and thus promote the propane dehydrogenation under heterogeneous catalysis.

The isothermal characteristics of the propane dehydrogenation under heterogeneous catalysis is further improved by mounting closed internals (e.g. annular ones) evacuated before they are filled in the tray reactor, in the spaces between the catalyst beds. Of course, such internals may also be positioned in the respective catalyst bed. These internals contain suitable solids or liquids which evaporate or melt above a specific temperature and thus consume heat and condense again where the temperature falls below this temperature and thereby evolve heat.

One possibility for heating the reaction gas mixture in stage A of the novel process to the required reaction temperature is to subject a part of the propane and/or $H_2$ contained therein to combustion by means of molecular oxygen (for example over suitable specific combustion catalysts, e.g. by simply passing over and/or passing through) and to effect heating to the desired reaction temperature by means of the heat of combustion thus evolved. The resulting combustion products, such as $CO_2$ and $H_2O$, and the $N_2$ which may accompany the molecular oxygen required for combustion, advantageously form inert diluent gases.

According to the invention, it is essential that the propane used in stage A is not pure propane. Rather, the propane used may contain up to 50% by volume other gases, such as ethane, methane, ethylene, butanes, butenes, propyne, acetylene, $H_2S$, $SO_2$, pentanes, etc. Expediently, the crude propane to be used contains at least 60, advantageously at least 70, preferably at least 80, particularly preferably at least 90, very particularly preferably at least 95, % by volume of propane. In particular, a mixture of propane, propylene and recycled gas originating from the oxidation stage may also be used for the novel stage A.

The product gas mixture leaving stage A in the novel process contains at least the components propane, propene and molecular hydrogen. Moreover, it generally also contains gases from the group consisting of $N_2$, $H_2O$, methane, ethane, ethylene, CO and $CO_2$.

As a rule, it has a pressure of from 0.3 to 10 atm and frequently a temperature of from 400 to 550° C., in advantageous cases from 450 to 500° C.

According to the invention, it is essential to separate off at least a part of the hydrogen contained in the product gas mixture A before the product gas mixture A' obtainable thereby is used in stage B for feeding at least the one oxidation reactor. This can be effected, for example by passing the product gas mixture A, if necessary after it has cooled in an indirect heat exchanger (expediently, the heat removed thereby is used for heating the feed gas required for the novel process), over a membrane which is generally formed into a tube and is permeable only to the molecular hydrogen. The molecular hydrogen separated off in this manner can, if required, be partly recycled to the stage A or otherwise utilized. In the simplest case it can be combusted in fuel cells.

Alternatively, the at least partial hydrogen separation which is required can also be carried out by partial condensation, adsorption and/or rectification (preferably under pressure).

According to the invention, as a rule at least 10 or at least 25, frequently at least 35 or at least 50, in many cases at least 75, mol % and often the total amount of the molecular hydrogen contained in the product gas mixture A is separated off before it is used as product gas mixture A' in stage B according to the invention for feeding the at least one oxidation reactor.

If required, other components of the product gas mixture A other than propane and propylene can of course be separated off in the course of removal of molecular hydrogen.

A simple possibility for separating off essentially all components of the product gas mixture A other than propane and propylene comprises bringing the preferably cooled product gas mixture A (preferably to temperatures of from 10 to 70° C.), for example at from 0.1 to 50 atm and from 0 to 100° C., into contact (for example by simply passing through) with a (preferably high-boiling) organic solvent (preferably hydrophobic), in which propane and propene are preferably absorbed. By a subsequent desorption, rectification and/or stripping with a gas which is inert with respect to the novel oxidation stage B and/or with molecular oxygen (e.g. air), the propane and propene in the mixture are recovered and are used for feeding the at least one oxidation reactor of stage B. The absorption exit gas containing the molecular hydrogen can, for example, be subjected to membrane separation again and then, if required, the hydrogen separated off can be concomitantly used in stage A. Preferably the boiling point of the organic absorbent should be $\geq 100°$ C., particularly $\geq 180°$ C. The absorption can be carried out both in columns and in rotary absorbers. The cocurrent or countercurrent method may be employed. Suitable absorption columns are, for example, tray columns (having bubble, centrifugal and/or sieve trays), columns having structured packings (e.g. sheet metal packings having a specific surface area with from 100 to 500 $m^2/m^3$, e.g. Mellapak® 250 Y) and columns having dumped packings (e.g. filled with Raschig packings). Of course, trickle and spray towers, graphite block absorbers, surface absorbers, such as thick-film and wetted-wall absorbers, and rotary columns, plate scrubbers, cross-film scrubbers and rotary scrubbers may also be used.

According to the invention, it is advantageous if the organic absorbent to be used fulfills the abovementioned recommendations for the boiling point on the one hand and, on the other hand, at the same time does not have too high a molecular weight. Advantageously, the molecular weight of the absorbent is $\leq 300$ g/mol.

Absorbents suitable according to the invention are, for example, relatively nonpolar organic solvents which preferably contain no externally active polar group. Examples are aliphatic (e.g. $C_8$- to $C_{18}$-alkanes) or aromatic hydrocarbons, for example middle oil fractions from paraffin distillation, or ethers having bulky groups on the O atom, or mixtures thereof, it being possible to add a polar solvent, e.g. 1,2-dimethyl phthalate disclosed in DE-A 4 308 087, to said relatively nonpolar solvents. Also suitable are esters of benzoic acid and phthalic acid with straight-chain alkanols of 1 to 8 carbon atoms, such as n-butyl benzoate, methyl benzoate, ethyl benzoate, dimethyl phthalate and diethyl phthalate, and heat-transfer oils, such as biphenyl, diphenyl ether and mixtures of biphenyl and diphenyl ether or their chlorine derivatives and triarylalkenes, e.g. 4-methyl-4'-benzyldiphenylmethane and its isomers 2-methyl-2'-benzyldiphenylmethane, 2-methyl-4'-benzyldiphenylethane and 4-methyl-2'-benzyldiphenylmethane and mixtures of such isomers. A suitable absorbent is a solvent mixture comprising biphenyl and diphenyl ether, preferably in the azeotropic composition, in particular comprising about 25% by weight of biphenyl and about 75% by weight of diphenyl ether, for example the commercially available Diphyl®. Frequently, this solvent mixture contains an added solvent such as dimethyl phthalate in an amount of from 0.1 to 25% by weight, based on the total solvent mixture. Octanes, nonanes, decanes, undecanes, dodecanes, tridecanes, tetradecanes, pentadecanes, hexadecanes, heptadecanes and octadecanes should also be mentioned as possible absorbents.

Finally, it should be pointed out the partial or complete separation of the molecular hydrogen from the product gas mixture A can also be carried out by selective combustion thereof with molecular oxygen under heterogeneous catalysis. Catalysts suitable in this respect are disclosed, for example, in U.S. Pat. Nos. 4,788,371, 4,886,928, 5,430,209, 5,530,171, 5,527,979 and U.S. Pat. No. 5,563,314.

In the at least partial separation of the molecular hydrogen contained in product gas mixture A, effected according to the invention, the product gas mixture A' obtained can be used in the second stage B, required according to the invention for feeding at least one oxidation reactor and, in the at least one oxidation reactor, the propylene can be subjected to a selective gas-phase partial oxidation with molecular oxygen under heterogeneous catalysis to give a product gas mixture B containing acrolein and/or acrylic acid. If required, the product gas mixture A' is brought beforehand, by indirect heat exchange, to the reaction temperature required in the at least one oxidation reactor.

In principle, the partial gas-phase oxidation of propylene to acrylic acid with molecular oxygen under heterogeneous catalysis takes place in two steps in succession along the reaction coordinates, of which the first leads to acrolein and the second from acrolein to acrylic acid.

This reaction sequence in two successive steps with respect to time opens up, in a manner known per se, the possibility of carrying out stage B of the novel process in two oxidation zones arranged one behind the other, it being possible for the oxidic catalyst to be used to be adapted in an optimizing manner to both oxidation zones. For example, as a rule a catalyst based on multimetal oxides containing the element combination Mo—Bi—Fe is preferred for the first oxidation zone (propylene acrolein) while catalysts based on multimetal oxides containing the element combination Mo—Bi—Fe are usually preferred for the second oxidation zone (acrolein→acrylic acid).

Corresponding multimetal oxide catalysts for the two oxidation zones have been widely described in the past and are well known to those skilled in the art. For example, page 5 of EP-A 253 409 refers to corresponding US patents.

Advantageous catalysts for the two oxidation zones are also disclosed in DE-A 4 431 957 and DE-A 4431949. This applies in particular to those of the formula I in the two abovementioned publications. As a rule, the product mixture in the first oxidation zone is transferred to the second oxidation zone without intermediate treatment.

The simplest implementation of the two oxidation zones is therefore a tube-bundle reactor within which the catalyst load changes along the individual catalyst tubes with the completion of the first reaction step (such partial propylene oxidations suitable as stage B according to the invention are described in, for example, EP-A 911313, EP-A 979813, EP-A 990636 and DE-A 2830765). If required, the catalyst load in the catalyst tube is interrupted by an inert bed.

However, the two oxidation zones are realized in the form of two tube-bundle systems connected in series. These may be present in a reactor, the transition from one tube bundle to the other tube bundle being formed by an (expediently accessible) bed of inert material which is not housed in the catalyst tube. While as a rule a heat-transfer medium flows around the catalyst tubes, said heat-transfer medium does not reach an inert bed installed as described above. The two catalyst tube bundles are therefore advantageously housed in reactors separated spatially from one another. As a rule, an intermediate condenser for reducing any acrolein postcombustion in the product gas mixture which leaves the first oxidation stage is present between the two tube-bundle reactors. Instead of tube-bundle reactors, it is also possible to use plate-type heat exchanger reactors with salt cooling and/or evaporator cooling, as described, for example, in DE-A 19 929 487 and DE-A 19 952 964.

The reaction temperature of the first oxidation zone is as a rule from 300 to 450° C., preferably from 320 to 390° C. The reaction temperature in the second oxidation zone is as a rule from 200 to 300° C., frequently from 220 to 290° C. The reaction pressure in the two oxidation zones is expediently from 0.5 to 5, advantageously from 1 to 3, atm. The loading (1 (S.T.P)Nl/l·h) of the oxidation catalysts with reaction gas in the two oxidation zones is frequently from 1500 to 2500 $h^{-1}$ and up to 4000 $h^{-1}$, respectively.

In principle, the two oxidation zones of the novel process can be designed as described, for example, in DE-A 19 837

517, DE-A 19 910 506, DE-A 19 910 508 and DE-A 19 837 519. Usually, the external heating of the two oxidation zones, if required in multizone reactor systems, is adapted in a manner known per se to the specific reaction gas mixture composition and catalyst load.

Molecular oxygen required altogether as oxidizing agent for stage B required according to the invention can be added in its entirety beforehand to the feed mixture of stage B. However, further oxygen can of course also be added after the first oxidation zone.

Preferably a molar propylene:molecular oxygen ratio of from 1:1 to 1:3, frequently from 1:1.5 to 1:2 is established in the first oxidation zone. The same numerical values are suitable for the molar acrolein:molecular oxygen ratio in the second oxidation zone.

In the two oxidation zones, an excess of molecular oxygen generally has an advantageous effect on the kinetics of the gas phase oxidation. In contrast to the conditions in stage A to be used according to the invention, the thermodynamic conditions are essentially not influenced by the molar reactant ratio since the partial gas-phase oxidation of the propylene to acrylic acid under heterogeneous catalysis is subject to kinetic control. In principle, the propylene too can therefore be initially taken in a molar excess relative to the molecular oxygen, for example in the first oxidation zone. In this case, the excess propylene in fact plays the role of a diluent.

In principle, however, the partial gas-phase oxidation of propylene to acrylic acid under heterogeneous catalysis can also be realized in a single oxidation zone. In this case, both reaction steps are carried out in an oxidation reactor which is loaded with a catalyst capable of catalyzing the reaction in both reaction steps. The catalyst load can of course also change continuously or abruptly along the reaction coordinates within the oxidation zone. In one embodiment of the stage B concomitantly to be used according to the invention and in the form of two oxidation zones connected in series, carbon monoxide, contained in the product gas mixture leaving the first oxidation zone and formed as a byproduct in the first oxidation zone, and steam can of course, if required, be partially or completely separated from said product gas mixture before further passage into the second oxidation zone. According to the invention, a procedure which does not require such a separation is preferably chosen.

Suitable sources for the molecular oxygen which is required in oxidation stage B and is mixed with product gas mixture A' before it is used for feeding oxidation stage B are both pure molecular oxygen and molecular oxygen diluted with inert gas, such as $CO_2$, CO, noble gas, $N_2$ and/or saturated hydrocarbons.

Expediently, air is used as an oxygen source at least for covering part of the molecular oxygen requirement, as in this way molecular nitrogen concomitantly to be used according to the invention in stage B can be introduced into the reaction system.

In the novel process, the product gas mixture A' advantageously comprises essentially only propane and propylene (the amount of components differing therefrom is expediently $\leq 5\%$ by volume or $\leq 2\%$ by volume, respectively) and exclusively air is used as a source of molecular oxygen for subsequent stage B.

By metering cold air into hot product gas mixture A', cooling of the product gas mixture A' can also be effected in a direct manner in the novel process.

If acrolein is the desired product, the second oxidation zone is expediently not used in stage B.

The product gas mixture B leaving the stage B to be used according to the invention is as a rule essentially composed of the desired product acrolein or acrylic acid or a mixture thereof with acrolein, unconverted molecular oxygen, propane, molecular nitrogen, steam formed as byproduct and/or present as diluent gas, oxides of carbon still present as byproduct and/or diluent gas, and small amounts of other lower aldehydes, hydrocarbons and other inert diluent gases.

The desired product can be separated from the product gas mixture B in a manner known per se (for example by partial condensation of the acrylic acid or absorption of acrylic acid in water or in a high-boiling hydrophobic organic solvent or by absorption of acrolein in water or in aqueous solutions of lower carboxylic acids and subsequent working-up of the absorbed substances; alternatively, the product gas mixture can also be subjected to fractional condensation; cf. for example EP-A 117146, DE-A 4308087, DE-A 4335172, DE-A 4436243, DE-A 19 924 532 and DE-A 19 924 533).

Unconverted propylene and/or acrolein are, if required, also separated off and recycled to stage B.

Otherwise, the major components other than acrylic acid and acrolein in residual gas remaining after isolation of the desired product can, depending on requirements and on the dehydrogenation catalyst used, be separated off by itself in each case and/or be recycled with propane as recycled gas to the dehydrogenation stage A in order to influence the dehydrogenation conversion there as described. However, the unconverted propane can of course also be recycled as a mixture with the unconverted propylene by itself to stage A. When the novel process is carried out continuously, continuous conversion of propane to acrylic acid and/or acrolein thus takes place.

The separation of propane and propene from the residual gas remaining after isolation of the desired product (said residual gas contains as a rule $O_2$, CO, $CO_2$, $H_2O$, $N_2$, noble gases and other lower aldehydes and hydrocarbons) can, as described above, be effected by absorption with subsequent desorption and/or stripping (and reuse of the absorbent) in a high-boiling hydrophobic organic solvent. Further possible methods of separation are adsorption, rectification and partial condensation.

With the use of dehydrogenation catalysts which are sensitive to oxygen or oxygen-containing compounds, these oxygen-containing substances can be separated from the recycled gas before the latter is recycled to stage A. Such an oxygen separation can also be useful in order to avoid oxidation of the propane in the dehydrogenation stage A. The dehydrogenation catalysts of DE-A 19 937 107 are not sensitive to oxygenates (in particular those according to Examples 1 to 4 of the DE-A).

Another possibility for separation is fractional distillation, as also stated above. Preferably, a fractional distillation under superatmospheric pressure at low temperatures is carried out. The pressure to be used may be, for example, from 10 to 100 bar. The rectification columns used may be columns containing dumped packings, tray columns or columns containing stacked packings. Suitable tray columns are those having dual-flow trays, bubble trays or valve trays. The reflux ratio may be, for example, from 1 to 10. Other possible methods of separation are, for example, extraction under pressure, pressure swing adsorption, scrubbing under pressure, partial condensation and extraction under pressure.

According to the invention, the total amount of residual gas can of course also be recycled to stage A. In this case, the outlet for gas components other than propane, propene and molecular oxygen may be present exclusively between product gas mixture A and product gas mixture A'.

A further outlet can of course be set up after the isolation of the desired product. If the recycled gas recycled to the propane dehydrogenation contains carbon monoxide, this can be catalytically incinerated to $CO_2$ before fresh propane is added. The heat of reaction evolved thereby can be used for heating to the dehydrogenation temperature.

A catalytic postcombustion of CO contained in the residual gas to give $CO_2$ may also be advisable when it is desired to separate oxides of carbon from residual gas before the latter is recycled as recycled gas to the propane dehydrogenation, since $CO_2$ can be separated off comparatively easily (for example by scrubbing with a basic liquid).

It is of course also possible to adopt a procedure in which a part of the residual gas is recycled unchanged to the propane dehydrogenation and only propane and propene are separated off as a mixture from the remaining part and are likewise recycled to the propane dehydrogenation and/or to stage B. In the latter case, the remaining part of the residual gas is expediently combined with product gas mixture A.

In a fractional distillation of the residual gas, the operating line can be positioned, for example, so that essentially all those components whose boiling point is lower than the boiling point of propene are separated off at the top of the rectification column. These components are primarily the oxides of carbon CO and $CO_2$ and unreacted oxygen and ethylene as well as methane and $N_2$ Frequently, the novel process is carried out in such a way that, in the product gas mixture B, at least 70, preferably at least 80, mol % of the molecular oxygen sent to the various reaction stages have undergone reaction.

In the novel process, a molar ratio of acrolein to molecular oxygen to steam to propane to molecular nitrogen to other diluents of 1: from 0.5 to 1: from 0.1 to 1: from 0.5 to 6: from 1 to 10: from 0 to 5 is preferably employed in the second oxidation zone of stage B.

The advantage, according to the invention, of reduced formation of the byproducts propionaldehyde and/or propionic acid is obtained essentially independently of which multimetal oxide catalysts are used in stage B concomitantly to be used according to the invention. It is also obtained essentially independently of whether the volume-specific catalyst activity in stage B is kept constant or is chosen to increase along the reaction coordinates.

In particular, the advantage according to the invention is obtained when multimetal oxide catalysts which correspond to those of the formula I or II or III from DE-A 19 910 506 are used in the first oxidation zone of stage B and when multimetal oxide catalysts which correspond to those of the formula I or I' or II of DE-A 19 910 508 are used in the second oxidation zone of stage B.

Catalyst geometries according to the invention for the first or second oxidation zone of stage B to be used according to the invention are those which are recommended in DE-A 19 910 506 or DE-A 19 910 508.

Moreover, regarding the flow of reaction gas and heating medium (e.g. salt bath), the tube-bundle reactors recommended for the novel stage B may be operated both by the cocurrent method and by the countercurrent method. Crossflows can of course also be superposed. A meandering flow of the heating medium around the catalyst tubes, which, when viewed over the reactor, can in turn take place cocurrently or countercurrently relative to the reaction gas mixture, is particularly advantageous.

As a rule, reactors having passivated inner surfaces are used for the novel stage A. The passivation can be effected, for example, by applying sintered alumina to the inner surface prior to the dehydrogenation. However, it may also be effected in situ by adding small amounts of passivating assistants (e.g. sulfides) to the reaction gas mixture.

EXAMPLES

A) Preparation of a Multimetal Oxide Catalyst for the First Oxidation Zone of Stage B 1. Preparation of a Starting Material 1

209.3 kg of tungstic acid (72.94% by weight W) were stirred a little at a time at 25° C. into 775 kg of an aqueous solution of bismuth nitrate (11.2% by weight of Bi, from 3 to 5% by weight of free nitric acid; density: from 1.22 to 1.27 g/ml). The resulting aqueous mixture was stirred for a further 2 hours at 25° C. and then spray-dried.

The spray-drying was carried out in a rotating-disk spray tower by the countercurrent method at a gas inlet temperature of 300±10° C. and a gas outlet temperature of 100±10° C. The spray-dried powder obtained was then calcined at from 780 to 810° C. (in a rotary tubular furnace through which air flowed (1.54 m³ internal volume, 200 m³ S.T.P. of air/h)). What is important with regard to the exact setting of the calcination temperature is that it must be based on the desired composition of the calcination product. The phases $WO_3$ (monoclinic) and $Bi_2W_2O_9$ are desired; the presence of γ-$Bi_2WO_6$ (russellite) is undesirable. If therefore, after the calcination the compound γ-$Bi_2WO_6$ is still detectable from a reflection in the powder X-ray diffraction pattern at a reflection angle of 2-=28.4° (CuKα-radiation), the preparation should be repeated and the calcination temperature should be increased within the stated temperature range until the reflection disappears. The preformed calcined mixed oxide thus obtained was milled so that the $X_{50}$ value (cf. Ullmann's Encyclopedia of Industrial Chemistry, 6th Edition (1998), Electronic Release, Section 3.1.4 or DIN 66141) of the resulting particle size distribution was 5 μm. The milled material was then mixed with 1% by weight (based on the milled material) of finely divided $SiO_2$ (bulk density 150 g/l; $X_{50}$ value of the $SiO_2$ particles was 10 μm, the BET surface area was 100 m²/g).

2. Preparation of Starting Material 2

A solution A was prepared by dissolving 213 kg of ammonium heptamolybdate in 600 l of water at 60° C. while stirring, and 0.97 kg of an aqueous potassium hydroxide solution (46.8% by weight of KOH) at 20° C. was added to the resulting solution and maintained at 60° C. while stirring.

A solution B was prepared by introducing 116.25 kg of an aqueous iron nitrate solution (14.2% by weight of Fe) into 262.9 kg of an aqueous cobalt nitrate solution (12.4% by weight of Co) at 60° C. The solution B was then pumped continuously into the initially taken solution A over a period of 30 minutes while maintaining the 60° C. Stirring was then carried out for 15 minutes at 60° C. Thereafter, 19.16 kg of a silica gel (46.80% by weight of $SiO_2$, density: from 1.36 to 1.42 g/ml, pH from 8.5 to 9.5, alkali content not more than 0.5% by weight) were added to the resulting aqueous mixture and stirring was then carried out for a further 15 minutes at 60° C.

Spray-drying was then carried out in a rotating-disk spray tower by the countercurrent method (gas inlet temperature: 400±10° C., gas outlet temperature: 140±5° C.). The resulting spray-dried powder had a loss on ignition of about 30% by weight (ignition for 3 hours at 600° C.).

3. Preparation of the Multimetal Oxide Active Material and of the Catalyst

The starting material 1 was homogeneously mixed with the starting material 2 in the amount required for the multimetal oxide active material having the stoichiometry

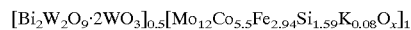

In addition, 1.5% by weight, based on the abovementioned total material, of finely divided graphite (sieve analysis: min. 50% by weight <24 μm, max. 10% by weight >24 μm and <48 μm, max. 5% by weight >48 μm, BET surface area:

from 6 to 13 m²/g) was homogeneously mixed in. The resulting dry mixture was molded to give hollow cylinders having a length of 3 mm, an external diameter of 5 mm and a wall thickness of 1.5 mm and then thermally treated as follows.

In a muffle furnace through which air flowed (60 l internal volume, 1 l (S.T.D)/h of air per gram of active precursor material), heating was effected initially from room temperature (25° C.) at a heating rate of 180° C./h to 190° C. This temperature was maintained for 1 hour and then increased to 210° C. at a heating rate of 60° C./h. The 210° C. were maintained for 1 hour before it was increased at a heating rate of 60° C./h to 230° C. This temperature was likewise maintained for 1 hour before it in turn was increased at 265° C. at a heating rate of 60° C./h. The 265° C. were then likewise maintained for 1 hour. Thereafter, initially cooling to room temperature was carried out, and the decomposition phase was thus essentially complete. Thereafter, heating was effected at a heating rate of 180° C./h to 465° C., and this calcination temperature was maintained for 4 hours. Unsupported catalyst rings V suitable for the first oxidation zone of stage B resulted.

B) Preparation of a Multimetal Oxide Catalyst for the Second Oxidation Zone of Stage B 1. Preparation of the Catalytically Active Oxide Material $Mo_{12}V_3W_{1.2}Cu_{2.4}O_n$ 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate were dissolved successively at 95° C. in 5500 g of water to give a solution II. Thereafter, solution I was stirred all at once into solution II and then a 25% strength by weight aqueous $NH_3$ solution was added until a solution formed again. This was spray-dried at an outlet temperature of 110° C. The resulting spray-dried powder was kneaded with 0.25 kg of a 30% strength by weight aqueous acetic acid solution per kg of powder using a type ZS1-80 kneader from Werner & Pfleiderer and then dried in a drying oven at 110° C. for 10 hours.

700 g of the catalyst precursor thus obtained were calcined in an air/nitrogen mixture [(200 l (S.T.P.) of $N_2$/15 l (S.T.P.) of air)/h] in a rotary tubular furnace (50 cm long, 12 cm internal diameter). During the calcination, the kneaded material was first heated continuously from room temperature (about 25° C.) to 325° C. in the course of one hour. This temperature was then maintained for 4 hours. Heating was then effected to 400° C. in the course of 15 minutes, this temperature was maintained for 1 hour and cooling to room temperature was then carried out.

The calcined catalytically active material was milled to give a finely divided powder, in which 50% of the powder particles passed through a sieve of mesh size from 1 to 10 μm and the proportion of particles having a maximum dimension above 50 μm as less than 1%.

2. Preparation of Coated Catalysts 28 kg of annular supports (7 mm diameter, 3 mm length, 4 mm internal diameter, steatite, having a surface roughness Rz according to EP-B 714700 of 45 μm and having a total pore volume, based on the volume of the supports, of ≦1% by volume, manufacturer: Ceramtec DE) were introduced into a coating pan (angle of inclination 90°; Hicoater from Lödige, Del.) having an internal volume of 200 l. The coating pan was then rotated at 16 rpm. 2000 g of an aqueous solution consisting of 75% by weight of $H_2O$ and 25% by weight of glycerol were then sprayed onto the supports via a nozzle in the course of 25 minutes. At the same time, 7.35 kg of the catalytically active oxide powder from a) were metered continuously via a vibrating channel outside the spray cone of the atomizer nozzle in the same period. During the coating, the powder fed in was completely adsorbed onto the surface of the support and no agglomeration of the finely divided oxidic active material was observed. After the end of the addition of powder and aqueous solution, hot air at 110° C. was blown into the coating pan at a speed of 2 rpm for 20 minutes. Drying was then carried out under air for a further 2 hours at 250° C. with the bed stationary (tray oven). Annular coated catalysts S which are suitable for the second oxidation zone of stage B and whose proportion of oxidic active material was 21% by weight, based on the total material were obtained. The coat thickness was 240±25 μm, both over the surface of one support and over the surface of different supports.

C) Loading a Reaction Tube System R Suitable for Stage B and Heating Said System 1. Loading a First Reaction Tube A reaction tube (V2A stainless steel; 30 mm external diameter; 2 mm wall thickness; 26 mm internal diameter, length; 439 cm, and having a thermal tube (6 mm diameter) centered in the middle of the reaction tube and intended for holding a thermocouple by means of which the temperature in the reaction tube can be determined) is loaded from bottom to top on a catalyst support (32 cm long) first with steatite beads having a rough surface (diameter from 4 to 5 mm; inert material for heating the reaction gas starting mixture) over a length of 30 cm. This is followed by a 100 cm long load which consists of a homogeneous mixture of 373 g of unsupported catalyst rings V from A) and 160 g of steatite rings measuring 5 mm×3 mm×2 mm (external diameter×length×wall thickness). The reaction tube loading is completed by first a 170 cm long bed of unsupported catalyst rings V from A) and then a 107 cm long bed of the abovementioned steatite beads having a rough surface (diameter from 4 to 5 mm).

2. Loading a Second Reaction Tube

A reaction tube (V2A stainless steel; 30 mm external diameter; 2 mm wall thickness; 26 mm internal diameter, length: 441 cm, and having a thermal tube (6 mm external diameter) centered in the middle of the reaction tube and intended for holding a thermocouple by means of which the temperature in the reaction tube can be determined) is loaded from bottom to top on a catalyst support (34 cm long) first with a coated catalyst S from B) over a length of 200 cm and then with a coated catalyst S' (prepared in the same way as the coated catalyst S but the amount of oxidic active material is chosen to be only 17% by weight, based on the total material) over a length of 100 cm. A 56 cm long load comprising steatite beads having a rough surface (diameter from 4 to 5 mm) terminates the reaction tube loading.

3. Connecting Tube

The first and second reaction tubes are connected to one another at their end opposite the respective catalyst support ledge by a connecting tube (V2A stainless steel; 1 m length; internal diameter 9 mm). The connecting tube has, in the middle, the possibility for adding a gas containing molecular oxygen.

4. Heating the Reaction Tube System

Pumped salt melts are used for heating the reaction tubes. The pumped salt melt of the first reaction tube is kept at X° C. The pumped salt melt of the second reaction tube is kept at Y° C. The connecting tube is kept at 200° C. (by means of electrical heating mats).

D) Carrying Out Gas-Pahse Oxidations

1. Composition of a Reaction Gas Mixture A 5.5% by volume of propene,
9.7% by volume of $O_2$,
10% by volume of $H_2O$ and
74.8% by volume of $N_2$.

2. Composition of a Reaction Gas Mixture B 5.5% by volume of propene,
9.7% by volume of $O_2$,
10% by volume of $H_2O$ and
74.8% by volume of propane.

3. Composition of a Reaction Gas Mixture C 5.5% by volume of propene,
9.7% by volume of $O_2$,
10% by volume of $H_2O$ and
37.8% by volume of propane and
37.0% by volume of $N_2$.

The reaction tube system from C) is fed in each case with the reaction gas mixture A or with the reaction gas mixture B or with the reaction gas mixture C. The reaction gas mixture is fed into the first reaction tube and in particular into the tube end having the catalyst support ledge.

The loading of the catalyst bed of the first reaction tube is chosen in each case to be 100 l (S.T.P.) of propene/l of catalyst h ($h^{-1}$). In the connecting tube, 75 l (S.T.P.)/h mixed in at room temperature are added in all three cases.

The thermostating of the reaction tube system is chosen so that, in all three cases, based on a single pass, a propene conversion of 94 mol % results in the first reaction tube and a conversion of 97.5 mol % of the acrolein formed in the first reaction tube results in the second reaction tube.

After an operating time of 10 hours, the product mixture leaving the second reaction tube is analyzed in each case to determine its content of propionic acid (based on the total content of acrylic acid).

The table below shows the results.

1. Reaction Gas Mixture A

X=328° C.
Y=270° C.
Content of propionic acid: 0.02 mol %.

2. Reaction Gas Mixture B

X=358° C.
Y=295° C.
Content of propionic acid: 0.14 mol %.

3. Reaction Gas Mixture C

X=343° C.
Y=281° C.
Content of propionic acid: 0.08 mol %.

This means that the propionic acid product formation is more than six times greater in case B than in case A, which shows that the use of molecular nitrogen as a diluent gas is capable of reducing the propionic acid byproduct formation.

E) Catalytic Postcombustion of CO to $CO_2$ in a Product Gas Mixture B) for Which the Desired Products Have Been Separated Off.

A gas mixture composed of 2.5% by volume of CO, 1% by volume of propene, 82% by volume of propane and 14,5% by volume of a mixture of $H_2O$, $N_2$ and $CO_2$ was passed, at 212° C. (heating was effected by means of an aluminum block resting on the reaction tube and heated by means of electrical heating mats), after the addition of 2 times the stoichiometric amount, based on CO, of molecular $O_2$ through a fixed bed (internal tube diameter: 20,5 mm, a thermal sleeve for an internal thermocouple and having an external diameter of 4 mm was centered in the tube, bed length: 19 cm) of the commercially available BASF noble metal catalyst RO 20 (beads having a diameter of 3 mm, $Al_2O_3$ as support, Pd as noble metal active component) (at a catalyst loading with gas mixture of 1680 $h^{-1}$). 94 mol % of the CO contained in the gas mixture were combusted to give $CO_2$. The other gas components remained essentially unchanged. A subsequent separation of propane and propene from the gas mixture by fractional distillation under pressure can now be carried out in a simpler manner.

We claim:

1. A process for the preparation of acrolein or acrylic acid or a mixture thereof from propane, in which A) in a first stage A, the propane is subjected to a partial dehydrogenation under heterogeneous catalysis in the gas phase with formation of a product gas mixture A which contains molecular hydrogen, propylene and unconverted propane, B) of the components contained in the product gas mixture A and differing from propane and propylene, at least a portion of the molecular hydrogen is separated off from said mixture A of stage A, containing molecular hydrogen, propylene and unconverted propane, the mixture is then used as product gas mixture A' in a second stage B for feeding at least one oxidation reactor and, in the at least one oxidation reactor, the propylene is subjected to a selective partial gas-phase oxidation with molecular oxygen under heterogeneous catalysis to give a product gas mixture B which contains acrolein or acrylic acid or a mixture thereof as the desired product, and C) in a third stage C, the desired product is separated off from the product gas mixture B obtained in the partial oxidation of the propylene in stage B and at least unconverted propane contained in the product gas mixture of stage B is recycled to the dehydrogenation stage A, wherein molecular nitrogen is present as diluent gas in the partial oxidation of the propylene in stage B.

2. A process as claimed in claim 1, wherein the feed gas mixture of the at least one oxidation reactor in the second stage B contains at least 5 mol %, based on propylene contained therein, of molecular nitrogen.

3. A process as claimed in claim 1, wherein the feed gas mixture of the at least one oxidation reactor in the second stage B contains at least 50 mol %, based on propylene contained therein, of molecular nitrogen.

4. A process as claimed in claim 1, wherein the feed gas mixture of the at least one oxidation reactor in the second stage B contains at least 100 mol %, based on propylene contained therein, of molecular nitrogen.

5. A process as claimed in claim 1, wherein the molar ratio of the amount of molecular nitrogen contained in the feed gas mixture of the at least one oxidation reactor in the second stage B to the amount of propane contained in the same feed gas mixture is at least 0.05.

6. A process as claimed in claim 1, wherein the molar ratio of the amount of molecular nitrogen contained in the feed gas mixture of the at least one oxidation reactor in the second stage B to the amount of propane contained in the same feed gas mixture is at least from 0.05 to 5.

7. A process as claimed in claim 1, wherein the molar ratio of the amount of molecular nitrogen contained in the feed gas mixture of the at least one oxidation reactor in the second stage B to the amount of propane contained in the same feed gas mixture is at least from 0.5 to 3.

8. A process as claimed in claim 1, wherein the composition of the feed gas mixture of the at least one oxidation reactor in the second stage B fulfills the following molar ratios:

propane:propene:$N_2$:$O_2$:$H_2O$: others=from 0.5 to 20: 1: from 0.1 to 40: from 0.1 to 10: from 0 to 20: from 0 to 1.

9. A process as claimed in claim 1, wherein the composition of the feed gas mixture of the at least one oxidation reactor in the second stage B fulfills the following molar ratios:

propane:propene:$N_2$:$O_2$:$H_2O$: others=from 2 to 10:1: from 0.5 to 20: from 0.5 to 5: from 0.01 to 10: from 0 to 1.

10. A process as claimed in claim 1, wherein the composition of the feed gas mixture of the at least one oxidation reactor in the second stage B fulfills the following molar ratios:

propane:propene:$N_2$:$O_2$:$H_2O$: others=from 3 to 6:1: from 1 to 10: from 1 to 3: from 0.1 to 2: from 0 to 0.5.

11. A process as claimed in claim 1, wherein the molar ratio of propylene contained in the product gas mixture A to molecular hydrogen contained in the product gas mixture A is $\leq 100$.

12. A process as claimed in claim 1, wherein the molar ratio of propylene contained in the product gas mixture A to molecular hydrogen contained in the product gas mixture A is $\leq 50$.

13. A process as claimed in claim 1, wherein the molar ratio of propylene contained in the product gas mixture A to molecular hydrogen contained in the product gas mixture A is $\leq 10$.

14. A process as claimed in claim 1, wherein the molar ratio of propylene contained in the product gas mixture A to molecular hydrogen contained in the product gas mixture A is $\geq 0.05$.

15. A process as claimed in claim 1, wherein the propane conversion achieved in stage A is from 5 to 25 mol %, based on a single pass.

16. A process as claimed in claim 1, wherein the propane conversion achieved in stage A is from 10 to 20 mol %, based on a single pass.

17. A process as claimed in claim 15, wherein the propane to be dehydrogenated is diluted in stage A with steam.

18. A process as claimed in claim 17, wherein the molar ratio of steam to propane to be dehydrogenated is from 0.1 to 2.

19. A process as claimed in claim 15, wherein molecular hydrogen is added to the propane to be dehydrogenated.

20. A process as claimed in claim 19, wherein the molar ratio of molecular hydrogen to propane to be dehydrogenated is >0 and $\leq 5$.

21. A process as claimed in claim 15, wherein the partial dehydrogenation of the propane under heterogeneous catalysis in stage A is carried out adiabatically.

22. A process as carried out in claim 15, wherein the partial dehydrogenation of the propane under heterogeneous catalysis in stage A is carried out in a fixed-bed reactor through which the flow is axial or radial.

23. A process as claimed in claim 15, wherein the partial dehydrogenation of the propane under heterogeneous catalysis in stage A is carried out in a tray reactor.

24. A process as claimed in claim 23, wherein the temperature of the reaction gas mixture throughout the tray reactor is 450 to 550° C.

25. A process as claimed in claim 23, wherein the tray reactor contains from 2 to 8 catalyst beds spatially in succession.

26. A process as claimed in claim 23, wherein molecular oxygen is added to the reaction gas mixture during the partial dehydrogenation of the propane under heterogeneous catalysis in stage A.

27. A process as claimed in claim 1, wherein the amount of molecular hydrogen present is separated off from product gas mixture A before it is further used as product gas mixture A'.

28. A process as claimed in claim 1, wherein the components other than propane and propylene are separated off from product gas mixture A before it is further used as product gas mixture A'.

29. A process as claimed in claim 1, wherein the components other than propane and propylene are separated off from the product gas mixture A by bringing the product gas mixture A into contact with an organic solvent, adsorbing the propane and propylene selectively therein, liberating them again by subsequent desorption, stripping or desorption and stripping, and using them as product gas mixture A' for feeding the at least one oxidation reactor in stage B.

30. A process as claimed in claim 1, wherein air is concomitantly used for feeding the at least one oxidation reactor of stage B.

31. A process as claimed in claim 1, wherein acrolein and/or acrylic acid contained in the product gas mixture B are separated off from said mixture, and at least a portion of the remaining residual gas is recycled to the dehydrogenation stage A.

32. A process as claimed in claim 28, wherein acrolein and/or acrylic acid contained in the product gas mixture B are separated off from said mixture, and the total amount of the remaining residual gas is recycled to the dehydrogenation stage A.

33. A process as claimed in claim 1, wherein acrolein and/or acrylic acid contained in the product gas mixture B are first separated off from said mixture, the components other than propane and propylene are separated off from the remaining residual gas, and the remaining propane and propene are recycled to the dehydrogenation stage A.

34. A process as claimed in claim 1, wherein stage B consists of two tube-bundle reactors connected in series.

35. A process as claimed in claim 23, wherein the tray reactor comprises at least one catalyst bed which catalyzes the combustion of hydrogen.

36. A process as claimed in claim 1, which is carried out as a process for the preparation of acrolein.

37. A process as claimed in claim 1, which is carried out as a process for the preparation of acrylic acid.

38. A process as claimed in claim 16, wherein the propane to be dehydrogenated is diluted in stage A with steam.

39. A process as claimed in claim 16, wherein molecular hydrogen is added to the propane to be dehydrogenated.

40. A process as claimed in claim 16, wherein the partial dehydrogenation of the propane under heterogeneous catalysis in stage A is carried out adiabatically.

41. A process as carried out in claim 16, wherein the partial dehydrogenation of the propane under heterogeneous catalysis in stage A is carried out in a fixed-bed reactor through which the flow is axial or radial.

42. A process as claimed in claim 16, wherein the partial dehydrogenation of the propane under heterogeneous catalysis in stage A is carried out in a tray reactor.

43. A process as claimed in claim 42, wherein the temperature of the reaction gas mixture throughout the tray reactor is 450 to 550 C.

44. A process as claimed in claim 42, wherein the tray reactor contains from 2 to 8 catalyst beds spatially in succession.

45. A process as claimed in claim 42, wherein molecular oxygen is added to the reaction gas mixture during the partial dehydrogenation of the propane under heterogeneous catalysis in stage A.

46. A process as claimed in claim 16, wherein the tray reactor comprises at least one catalyst bed which catalyzes the combustion of hydrogen.

47. A process as claimed in claim 1, wherein the partial dehydrogenation of the propane under heterogeneous catalysis in stage A is carried out adiabatically.

48. A process as carried out in claim 1, wherein the partial dehydrogenation of the propane under heterogeneous catalysis in stage A is carried out in a fixed-bed reactor through which the flow is axial or radial.

49. A process as claimed in claim 1, wherein the partial dehydrogenation of the propane under heterogeneous catalysis in stage A is carried out in a tray reactor.

* * * * *